(12) United States Patent
Amrhein et al.

(10) Patent No.: US 8,999,358 B2
(45) Date of Patent: *Apr. 7, 2015

(54) AQUEOUS INSECTICIDAL COMPOSITIONS AND THE USE THEREOF FOR PROTECTING LIGNOCELLULOSE-CONTAINING MATERIALS

(75) Inventors: Patrick Amrhein, Hochheim (DE); Gunnar Kleist, Baden-Baden (DE); Dirk Haentzschel, Langenburg (DE); Joerg Habicht, Sinzheim (DE); Holger Schöpke, Neckargermünd (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 662 days.

This patent is subject to a terminal disclaimer.

(21) Appl. No.: 11/885,799

(22) PCT Filed: Mar. 8, 2006

(86) PCT No.: PCT/EP2006/002143

§ 371 (c)(1),
(2), (4) Date: Sep. 6, 2007

(87) PCT Pub. No.: WO2006/094792

PCT Pub. Date: Sep. 14, 2006

(65) Prior Publication Data

US 2008/0138371 A1 Jun. 12, 2008

(30) Foreign Application Priority Data

Mar. 9, 2005 (DE) .......................... 10 2005 010 874

(51) Int. Cl.
| | |
|---|---|
| A01N 25/04 | (2006.01) |
| A01N 53/02 | (2006.01) |
| A01N 47/10 | (2006.01) |
| A01N 57/10 | (2006.01) |
| A01N 43/36 | (2006.01) |
| A01P 7/04 | (2006.01) |
| A01N 25/26 | (2006.01) |
| A01N 25/28 | (2006.01) |
| A01N 53/00 | (2006.01) |
| B27K 3/00 | (2006.01) |
| B27K 3/15 | (2006.01) |

(52) U.S. Cl.
CPC .............. *A01N 43/36* (2013.01); *A01N 25/04* (2013.01); *A01N 25/26* (2013.01); *A01N 25/28* (2013.01); *A01N 53/00* (2013.01); *B27K 3/007* (2013.01); *B27K 3/15* (2013.01)

(58) Field of Classification Search
CPC ... A01N 2300/00; A01N 43/36; A01N 53/00; A01N 25/04; A01N 25/26; A01N 25/28; B27K 3/007; B27K 3/15; C08L 33/08; C08L 35/02

See application file for complete search history.

(56) References Cited

U.S. PATENT DOCUMENTS

| | | | |
|---|---|---|---|
| 3,400,093 | A | 9/1968 | Feinberg |
| 5,049,383 | A | 9/1991 | Huth et al. |
| 6,559,236 | B1 | 5/2003 | Willimann et al. |
| 6,765,072 | B1 | 7/2004 | Willimann et al. |
| 2002/0192259 | A1 * | 12/2002 | Voris et al. ................ 424/411 |

FOREIGN PATENT DOCUMENTS

| | | |
|---|---|---|
| CA | 2562347 A1 | 11/2005 |
| CN | 1491541 A | 4/2004 |
| EP | 0 161 881 A2 | 11/1985 |
| EP | 0 286 009 A2 | 10/1988 |
| EP | 1230855 * | 11/2000 ............ A01N 25/04 |
| JP | 60-250016 A | 12/1985 |
| WO | WO-00/05276 A1 | 2/2000 |
| WO | WO-00/05283 A1 | 2/2000 |
| WO | WO 03/039249 A2 | 5/2003 |
| WO | WO 03/039254 A1 | 5/2003 |
| WO | WO-2005/102044 A1 | 11/2005 |
| WO | WO-2006/015791 A2 | 2/2006 |

OTHER PUBLICATIONS

Cyhalothrin MSDS (Syngenta, revised Mar. 31, 2005).*
Methylmethacrylate registry proterty data as accessed by STN Dec. 12, 2008.*
Ullmann's Encyclopedia of E.H. Pommer, "Wood Preservation", Ch. 2, in Ullmann's Encyclopedia of Industrial Chemistry, 5th ed. on CD ROM, Wiley-VCH Weinheim 1997, vol. A28, pp. 357-383, 1996 VCH Verlagsgesellschaft.
Liu et al., "Controlled Release of Biocides in Solid Wood. III. Efficacy Against *Trametes versicolor* and *Gloeophyllum trabeum* Wood Decay Fungi", Journal of Applied Polymer Science, vol. 86, pp. 608-614, 2002.
Liu et al., "Controlled Release of Biocides in Solid Wood. III. Preparation and Characterization of Surfactant-Free Nanoparticles", Journal of Applied Polymer Science, vol. 86, pp. 615-621, 2002.

* cited by examiner

*Primary Examiner* — Kortney L Klinkel
(74) *Attorney, Agent, or Firm* — Birch, Stewart, Kolasch & Birch, LLP

(57) ABSTRACT

The present invention relates to aqueous insecticidal preparations in the form of an aqueous dispersion of finely divided polymer particles which comprise at least one insecticidal organic active ingredient with a solubility in water of not more than 5 g/l at 25° C. at 1013 mbar and which have a mean particle size, determined by dynamic light scattering, of not more than 300 nm, where the polymer particles which comprise the at least one insecticidal active ingredient of a cationic surface charge and where the aqueous dispersion of the active-ingredient-comprising polymer particles is obtainable by subjecting a monomer composition of ethylenically unsaturated monomers M, in which the ethylenically unsaturated monomers M comprise the at least one insecticidal active ingredient in dissolved form, to radical aqueous emulsion polymerization. The invention also related to the use of such aqueous insecticide compositions for protecting lignocellulosic materials, in particular timber, against attack by harmful insects.

14 Claims, No Drawings

AQUEOUS INSECTICIDAL COMPOSITIONS AND THE USE THEREOF FOR PROTECTING LIGNOCELLULOSE-CONTAINING MATERIALS

FIELD OF INVENTION

The present invention relates to aqueous insecticide compositions in the form of an aqueous dispersion of finely divided polymer particles which comprise at least one insecticidal organic active ingredient with a solubility in water of not more than 5 g/l at 25° C. at 1013 mbar and to the use of such aqueous insecticide compositions for the protection of lignocellulosic materials, in particular timber, against attack by harmful insects.

BACKGROUND OF INVENTION

As is known, materials based on lignocellulosic materials, in particular timber-based materials, are at risk from attack by harmful insects, for example wood-destroying beetles, ants and/or termites. Since attack can lead to damage and, in extreme cases, to complete destruction of the material, a great deal of effort goes into protecting such materials against such an attack.

Traditional timber preservatives which are based on tar oils, such as carbolineum, are not very attractive because of their intrinsic odor and the possibility of being carcinogens. This is why defined organic active ingredients are nowadays being employed for this purpose. Since these active ingredients are usually substances which are insoluble in water, they are, as a rule, formulated as solutions in organic solvents (see Ullmann's Encyclopedia of E. H. Pommer, "Wood, Preservation" Chapter 2, in Ullmann's Encyclopedia of Industrial Chemistry, 5th ed. on CD-ROM, Wiley-VCH Weinheim 1997). However, the use of solvents entails additional costs and moreover undesired for reasons of work hygiene and for environmental reasons. Moreover, there is the risk of the active ingredients being leached under atmospheric influences so that the resistance to atmospheric corrosion of such insecticidal finishes is frequently not satisfactory.

U.S. Pat. No. 3,400,093 discloses aqueous, insecticide-comprising polymer dispersions which are prepared by emulsion polymerization of ethylenically unsaturated monomers, where the monomers employed for the polymerization comprise a dissolved water-insoluble insecticidal active ingredient. The insecticide-comprising polymer dispersions described therein are employed for the preparation of water-based coating compositions such as dispersion paints and are intended to ensure an insecticidal finish of the coating. These polymer dispersions, however, are not suitable for the protection of timber.

The earlier German patent application 102004020332.6 describes aqueous active ingredient preparation comprising at least one fungicidal organic active ingredient with a solubility in water of not more than 5 g/l at 25° C. at 1013 mbar and a finely divided polymer with a mean particle size, determined by dynamic light scattering, of not more than 300 nm, where the polymer particles of the finely divided polymer comprise the active ingredient and where the polymer consists predominantly of ethylenically unsaturated monomers with a solubility in water or not more than 30 g/l at 25° C. These active ingredient compositions are suitable for protecting timber against wood-damaging fungi.

The earlier German patent application 102004037850.9 describes aqueous active ingredient compositions comprising at least one organic crop protectant, for example an insecticidal, fungicidal, acaricidal or herbicidal active ingredient, with a solubility in water of not more than 5 g/l at 25° C. at 1013 mbar and a finely divided polymer, where the active ingredient compositions are obtainable by a multi-step emulsion polymerization method in an aqueous suspension of the solid active ingredient particles, where the active ingredient particles in the suspension have a mean particle size, determined by dynamic light scattering, of not more than 1200 nm. This gives polymer/active ingredient particles in which the particle-shaped active ingredient is present in a form where it is coated by the emulsion polymer.

SUMMARY OF INVENTION

The present invention is thus based on the technical problem of providing aqueous compositions of insecticidal active ingredients which are sparingly soluble in water, i.e. which are soluble in water to less than 5 g/l, in particular less than 1 g/l, at 25° C. at 1013 mbar, said composition being advantageously suitable for protecting lignocellulosic materials, in particular timber, against attack by wood-damaging insects. In particular, the compositions should only comprise small amounts of, or no, volatile organic compounds such as organic solvents. Moreover, the active ingredient should not, or not substantially, be leached from the treated materials even when exposed to water. Furthermore, the aqueous active ingredient compositions should be more stable than conventional suspensions or microemulsions of organic active ingredients.

Surprisingly, it has been found that this technical problem is solved by an aqueous active ingredient composition in which the insecticidal active ingredient which is not, or only sparingly, soluble in water is present in the polymer particles of finely divided polymer which is insoluble in water and whose polymer particles have a mean particle size, determined by dynamic light scattering, of not more than 500 nm and a cationic surface charge, and where the aqueous dispersion of the active-ingredient-comprising polymer particles is obtainable by subjecting a monomer composition of ethylenically unsaturated monomers M, wherein the ethylenically unsaturated monomers M comprise the at least one insecticidal active ingredient in dissolved form, to radical aqueous emulsion polymerization.

The invention thus relates to an insecticide composition in the form of an aqueous dispersion of finely divided polymer particles which comprise at least one insecticidal organic active ingredient with a solubility in water of not more than 5 g/l at 25° C. at 1013 mbar and which have a mean particle size, determined by dynamic light scattering, of not more than 500 nm, in particular not more than 300 nm, where the polymer particles, which comprise the at least one insecticidal active ingredient, have a cationic surface charge and where the aqueous dispersion of the active-ingredient-comprising polymer particles is obtainable by subjecting a monomer composition of ethylenically unsaturated monomers M, in which the ethylenically unsaturated monomers M comprise the at least one insecticidal active ingredient in dissolved form, to radical aqueous emulsion polymerization.

The compositions according to the invention take the form of stable aqueous preparations of insecticidal active ingredients which are not, or only sparingly, soluble in water, which preparations are, in principle, suitable for all applications where it is desired to achieve an effective protection of materials against attack by harmful insects, such as wood-damaging beetles, ants or termites. Despite the fact that insecticidal organic active ingredient is incorporated into a polymeric matrix, the application rate of active ingredient required for effective protection is not higher, and in some cases indeed lower, than when using conventional solvent-based active ingredient preparations. Moreover, the penetration of the active ingredient into the lignocellulosic material is improved, so that the protection is retained even when the surface of the material is worked or destroyed. Moreover, these compositions result in an insecticidal finishing of materials which is distinguished by a high stability to atmospheric influences and which tend less to leaching. The present invention therefore also relates to the use of such aqueous compositions for controlling insects, in particular for controlling wood-damaging insects such as termites, ants and wood-destroying beetles. Here and in the following, the term control/controlling comprises preventing or avoiding attack by harmful insects and also the destruction of the insects in attack materials.

The composition according to the invention are particularly suitable for controlling harmful insects in timber and other lignocellulosic materials and in particular for protecting these materials against attack by harmful insects. A particular embodiment of the invention therefore relates to the use of such compositions for protecting lignocellulosic materials, in particular timber, against attack by harmful insects, in particular against attack by wood-damaging insects such as wood-damaging beetles, ants or termites, and the destruction of the harmful insects in attacked material.

However, the aqueous compositions according to the invention are also suitable for other applications in which it is desired to control harmful insects, for example in crop protection for controlling plant-injurious insects, in the treatment of seed and as soil treatment compositions.

DETAILED DESPCRITION OF INVENTION

The particle sizes stated herein, of the finely divided polymer, are weight-average particle sizes as they can be determined by dynamic light scattering. Methods in this context are known to the skilled worker, for example from H. Wiese in D. Distler, Wässrige Polymerdispersionen [Aqueous polymer dispersions], Wiley-VCH 1999, Chapter 4.2.1, p. 40 et seq. and literature cited therein, and H. Auweter, D. Horn, J. Colloid Interf. Sci. 105 (1985) 399, D. Lilge, D. Horn, Colloid Polym. Sci. 269 (1991) 704 or H. Wiese, D. Horn, J. Chem. Phys. 94 (1991) 6429. The mean particle size is generally in the range of from 10 to 300 nm, in particular in the range from 20 to 250 nm, especially preferably in the range of from 30 to 200 nm, and very especially preferably in the range from 30 to 150 nm.

In the compositions according to the invention, the polymer particles have a positive surface charge, i.e. they have, on their surface, positive charges which compensate for any negative charges which may be present. As is known, such a surface charge can be achieved for example by the monomers M to be polymerized comprising cationic monomers and/or monomers with at least one group which is capable of being protonated in water (monomers M-k). As is known, a positive surface charge can also be achieved by carrying out the emulsion polymerization in the presence of surface-active substances such as surfactants and protective colloids which, in turn, are positively charged and/or have at least one functional group which is capable of being protonated in water (cf. U.S. Pat. No. 5,874,524). Such substances are hereinbelow also referred to as surface-active substances O-k. Naturally, the cationic monomers M-k, or monomers M-k which are capable of being protonated in water, and/or the surface-active substances O-k will be employed in such an amount that the positive charges of these substances which are hereby introduced dominate over any negative charges or acidic groups, i.e. groups capable of being deprotonated, in the monomers employed for the polymerization and surface-active substances. Without wanting to be bound by theory, it is assumed that the insecticidal organic active ingredient which is not, or sparingly, soluble in water is present, in the compositions according to the invention, in finely divided form in the polymer matrix formed by the monomers M. The surface charge can be estimated via the ratio of total amount of polymerized monomers M and active ingredient relative to the total amount of cationic monomers M-k and surface-active substances O-k, minus monomers with acid groups and minus anionic surface-active substances. The monomers M-k, or the surface-active substance, are preferably employed in such an amount that the excess of cationic charges, or basic groups in the polymer, amounts to at least 0.02 mol per kg of polymer+active ingredient, and in particular in the range of from 0.05 to 1.5 mol per kg of polymer+active ingredient.

The values stated herein for the excess of cationic charges correspond to the difference between the amount of cationic charge which results from the cationic, or basic, constituents of the polymer and the amount of anionic charge, which results from the anionic, or acidic, constituents of the polymer. The excess cationic charge equals the cationic surface charge. Cationic, or basic, constituents of the polymer are here both the cationic, or basic, monomers employed for the preparation and cationic, or basic, surface-active substances. Accordingly, anionic constituents of the polymer are both the anionic, or acidic, monomers employed for the preparation and the anionic, or acidic, surface-active substances.

Suitable monomers M are, in principle, all ethylenically unsaturated monomers which can be polymerized by an aqueous emulsion polymerization method. As a rule, the monomer mixture thus comprises predominantly monoethylenically unsaturated monomers which are not, or sparingly, soluble in water, i.e. whose solubility in water amounts to not more than 30 g/l (at 25° C. and 1013 mbar). These monomers are hereinbelow also referred to as monomers M1. In particular, the solubility in water of the monomers M1 under these conditions is 0.1 to 20 g/l. They usually account for at least 60% by weight, in particular for at least 70% by weight, preferably for at least 80% by weight, for example for 60 to 100% by weight, preferably for 70 to 99.5% by weight, in particular for 75 to 99.5% by weight, especially preferably for 80 to 99% by weight and specifically for 90 to 98% by weight of the monomers M.

The monomers M1 include vinyl-aromatic monomers such as styrene, α-methylstyrene, tert-butylstyrene and vinyltoluene, esters of α,β-monoethylenically unsaturated mono- and dicarboxylic acids having 3 to 8 and in particular 3 or 4 C atoms with $C_1$-$C_{10}$-alkanols or with $C_5$-$C_8$-cycloalkanols, in particular the esters of acrylic acid, of methacrylic acid, of crotonic acid, the diesters of maleic acid, of fumaric acid and of itaconic acid and especially preferably the esters of acrylic acid with $C_2$-$C_{10}$-alkanols (=$C_2$-$C_{10}$-alkyl acrylates) such as ethyl acrylate, n-butyl acrylate, isobutyl acrylate, tert-butyl acrylate, n-hexyl acrylate, 2-ethylhexyl acrylate and 3-propylheptyl acrylate, and the esters of methacrylic acid with $C_1$-$C_{10}$-alkanols such as methyl methacrylate, ethyl methacrylate, n-butyl methacrylate, isobutyl methacrylate, tert-butyl methacrylate, n-hexyl methacrylate and the like. Moreover, suitable monomers M1 are vinyl and allyl esters of aliphatic carboxylic acids having 3 to 10 C atoms, for example vinyl propionate, and the vinyl esters of the Versatic® acids (vinyl versatates), vinyl halides such as vinyl chloride and vinylidene chloride, conjugated diolefins such as butadiene and isoprene, and $C_2$-$C_6$-olefins such as ethylene, propene, 1-butene and n-hexene. Preferred monomers M1 are vinyl-aromatic monomers, $C_2$-$C_{10}$-alkyl acrylates, in particular $C_2$-$C_8$-alkyl acrylates, specifically tert-butyl acrylate, and $C_1$-$C_{10}$-alkyl methacrylates and in particular $C_1$-$C_4$-alkyl methacrylates. In particular, at least 50% by weight of the monomers M1 are selected from among vinyl-aromatic monomers, in particular styrene, esters of methacrylic acid with $C_1$-$C_4$-alkanols, in particular methyl methacrylate and tert-butyl acrylate, and up to 50% by weight of the monomers M1 are selected from among other monomers M1, specifically among $C_2$-$C_8$-alkyl acrylates. Especially preferred monomers M1 are vinyl-aromatic monomers, specifically styrene, and mixtures of vinyl-aromatic monomers with the abovementioned $C_2$-$C_8$-alkyl acrylates and/or $C_1$-$C_4$-alkyl methacrylates, in particular those mixtures in which vinyl aromatics account for at least 60% by weight, e.g. from 60 to 95% by weight, based on the total amount of the monomers M1.

Other especially preferred monomers M1 are $C_1$-$C_4$-alkyl methacrylates, specifically methyl methacrylate, and mixtures of $C_1$-$C_4$-alkyl methacrylates with $C_2$-$C_4$-alkyl acrylates and/or vinyl-aromatics, in particular mixtures with a $C_1$-$C_4$-alkyl methacrylate content, specifically methyl methacrylate content, of at least 60% by weight, for example 60 to 95% by weight, based on the total amount of the monomers M1.

In a first embodiment of the invention, the monomers M therefore comprise at least one monoethylenically unsaturated monomer M-k which has at least one cationic group and/or at least one group which is capable of being protonated in aqueous environments. The amount of monomer M-k will then be typically in the range of from 0.1 to 30% by weight, in particular in the range of from 0.5 to 20% by weight, and specifically in the range of from 1 to 15% by weight, based on the total amount of the monomers M.

Suitable monomers M-k are those which have an amino group which is capable of being protonated, a quaternary ammonium group, an imino group which is capable of being protonated or a quaternized imino group. Examples of monomers which have an imino group which is capable of being protonated are N-vinylimidazole and vinylpyridines. Examples of monomers which have a quaternized imino group are N-alkylvinylpyridinium salts and N-alkyl-N'-vinylimidazolinium salts such as N-methyl-N'-vinylimidazolinium chloride or metosulfate.

Preferred among the monomers M-k are, in particular, the monomers of the formula I

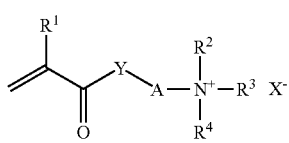

(I)

in which
$R^1$ is hydrogen or $C_1$-$C_4$-alkyl, in particular hydrogen or methyl,
$R^2$, $R^3$ independently of one another are $C_1$-$C_4$-alkyl, in particular methyl, and
$R^4$ is hydrogen or $C_1$-$C_4$-alkyl, in particular hydrogen or methyl,
Y represents oxygen, NH or $NR^5$ where $R^5$=$C_1$-$C_4$-alkyl,
A represents $C_2$-$C_8$-alkylene, for example 1,2-ethanediyl, 1,2- or 1,3-propanediyl, 1,4-butanediyl or 2-methyl-1,2-propanediyl which is optionally interrupted by 1, 2 or 3 non-adjacent oxygen atoms, and
$X^-$ represents an anion equivalent, for example halides such as $Cl^-$, $BF_4^-$, $HSO_4^-$, $\frac{1}{2}SO_4^{2-}$ or $CH_3OSO_3^-$ and the like, and for $R^4$=H the free bases of the monomers of the formula I.

Examples of monomers of the formula I are 2-(N,N-dimethylamino)ethyl acrylate, 2-(N,N-dimethylamino)ethyl methacrylate, 2-(N,N-dimethylamino)ethylacrylamide, 3-(N,N-dimethylamino)propylacrylamide, 3-(N,N-dimethylamino)propylmethacrylamide, 2-(N,N-dimethylamino)ethylmethacrylamide, 2-(N,N,N-trimethylammonium)ethyl acrylate chloride, 2-(N,N,N-trimethylammonium)ethyl methacrylate chloride, 2-(N,N,N-trimethylammonium)ethylmethacrylamide chloride, 3-(N,N,N-trimethylammonium)propylacrylamide chloride, 3-(N,N,N-trimethylammonium)propylmethacrylamide chloride, 2-(N,N,N-trimethylammonium)ethylacrylamide chloride, and the corresponding hydrogensulfates, metosulfates, tetrafluoroborates and sulfates.

Besides the monomers M1 and besides the monomers M-k which may if appropriate be present, the monomers M may also comprise other ethylenically unsaturated monomers M2. The monomers M2 include:

monoethylenically unsaturated monomers M2a which have at least one acid group or at least one anionic groups, in particular monomers M2a which have one sulfonic acid group, one phosphonic acid group or one or two carboxylic acid groups, and the salts of the monomers M2a, in particular the alkali metal salts, for example the sodium or potassium salts, and the ammonium salts. The monomers M2a include ethylenically unsaturated sulfonic acid, in particular vinylsulfonic acid, 2-acrylamido-2-methylpropanesulfonic acid, 2-acryloxyethanesulfonic acid and 2-methacryloxyethanesulfonic acid, 3-acryloxy- and 3-methacryloxypropane-sulfonic acid, vinylbenzenesulfonic acid and their salts, ethylenically unsaturated phosphonic acids such as vinylphosphonic acid and dimethyl vinylphosphonate and their salts, and α,β-ethylenically unsaturated $C_3$-$C_8$-mono- and $C_4$-$C_8$-dicarboxylic acids, in particular acrylic acid, methacrylic acid, crotonic acid, maleic acid, fumaric acid and itaconic acid. The monomers M2a will frequently not account for more than 10% by weight, preferably not for more than 5% by weight, for example for 0.1 to 10% by weight and in particular for 0.2 to 5% by weight, based on the total amount of the monomers M, the amount of the monomers M2a being selected in such a way that the anionic charge contributed by the monomers M2a does not exceed the cationic charge contributed by the surface-active substances, or the monomers M-k. In a particularly preferred embodiment, the monomers M comprise no, or less than 0.1% by weight of, monomers M2a;

monoethylenically unsaturated, neutral monomers M2b which have a solubility in water of at least 50 g/l at 25° C. and in particular at least 100 g/l at 25° C. Examples are the amides of the abovementioned ethylenically unsaturated carboxylic acids, in particular acrylamide and methacrylamide, ethylenically unsaturated nitriles such as methacrylonitrile and acrylonitrile, hydroxyalkyl esters of the abovementioned α,β-ethylenically unsaturated $C_3$-$C_8$-monocarboxylic acids and of the $C_4$-$C_8$-dicarboxylic acids, in particular hydroxyethyl acrylate, hydroxyethyl methacrylate, 2- and 3-hydroxypropyl acrylate, 2- and 3-hydroxypropyl methacrylate, esters of the abovementioned monoethylenically unsaturated mono- and dicarboxylic acids with $C_2$-$C_4$-polyalkylene glycols, in particular the esters of these carboxylic acids with polyethylene glycol or with alkylpolyethylene glycols, the (alkyl)polyethylene glycol residue usually having a molecular weight in the range of from 100 to 3000. The monomers M2b furthermore include N-vinylamides of aliphatic $C_1$-$C_{10}$-carboxylic acids, and N-vinyl lactams, such as N-vinylformamide, N-vinylacetamide, N-vinylpyrrolidone and N-vinyl caprolactam. The monomers M2b will preferably not account for more than 30% by weight and in particular not for more than 20% by weight, for example for 0.1 to 20 and in particular for 0.5 to 10% by weight, based on the total amount of the monomers M;

monomers M2c which have two or more nonconjugated ethylenically unsaturated double bonds. They will usually not account for more than 5% by weight, in particular not for more than 2% by weight, for example for 0.01 to 2% by weight and in particular for 0.05 to 1.5% by weight, based on the total amount of monomers M. In an especially preferred embodiment, the monomers M comprise no, or less than 0.05% by weight of, monomers M2c.

Furthermore, it has proved advantageous for the polymer comprised in the compositions according to the invention to have a glass transition temperature $T_g$ of at least 10° C., preferably at least 20° C., in particular at least 30° C. and specifically at least 50° C. In particular, the glass transition temperature will not exceed a value of 180° C. and especially preferably 130° C. If the active ingredient composition according to the invention comprises a plurality of polymers with different glass transition temperatures—be it in the form of step-growth, or core-shell polymers, including multiphase polymers with blackberry, raspberry or half-moon morphology, or in the form of blends of different polymers—, polymers with a glass transition temperature of at least 10° C., preferably at least 20° C., in particular at least 30° C. and specifically at least 50° C. account for at least 40% by weight.

The glass transition temperature $T_g$ is understood as meaning, according to ASTM D 3418-82, in the present context, the midpoint temperature determined by differential scanning calorimetry (DSC) (cf. Ullmann's Encyclopedia of Industrial Chemistry, 5th Edition, Volume A 21, VCH Weinheim 1992, p. 169, and Zosel, Farbe und Lack 82 (1976), pp. 125-134, see also DIN 53765).

In this context, it is helpful to estimate the glass transition temperature $T_g$ of the copolymer P. According to Fox (T. G. Fox, Bull. Am. Phys. Soc. (Ser. II) 1, 123 [1956] and Ullmanns Enzyklopädie der technischen Chemie, Weinheim (1980), pp. 17-18), a good approximation of the glass transition temperature of weakly crosslinked copolymers of high molecular weights is given by the equation $$\frac{1}{T_g} = \frac{X^1}{T_g^1} + \frac{X^2}{T_g^2} + \ldots \frac{X^n}{T_g^n}$$

where $X^1, X^2, \ldots, X^n$ denote the mass fractions of the monomers 1, 2, ..., n and $T_g^1, T_g^2, \ldots, T_g^n$ the glass transition temperatures of the polymers constructed in each case only of one of the monomers 1, 2, ..., n in degrees Kelvin. The aforementioned polymers are known for example from Ullmann's Encyclopedia of Industrial Chemistry, VCH, Weinheim, Vol. A 21 (1992) p. 169 or from J. Brandrup, E. H. Immergut, Polymer Handbook 3rd ed., J. Wiley, New York 1989.

The at least one insecticidal active ingredient may be essentially uniformly distributed in the polymer particles of the insecticide compositions according to the invention. However, the polymer particles may also contain zones with different active ingredient concentrations. In such a case, the zones with high active ingredient concentrations and the zones with low active ingredient concentrations may be in the form of a core-shell arrangement (core-shell morphology), in the form of droplet- or sphere-shaped zones which penetrate each other in part (half-moon morphology) or which are, if appropriate, embedded in a matrix or arranged on a polymer matrix (blackberry or raspberry morphology).

In a preferred embodiment of the invention, the polymer particles contain zones with high active ingredient concentrations and zones with low active ingredient concentrations, where the former are arranged in the outer zones and the latter in the inner zones of the polymer particles. For example, the zones with higher concentrations form an uninterrupted or interrupted shell around a core with a lower active ingredient concentration, or the zones with higher concentrations form droplets or spheres, the major part of which being arranged on a core zone with a lower concentration or embedded into the surface of this core zone.

The zones with higher active ingredient concentrations preferably comprise at least 60% by weight, in particular at least 80% by weight and up to 100% by weight, of the insecticidal active ingredient present in the composition, whereas the zones with lower active ingredient concentrations will typically comprise no more than 40% by weight, frequently no more than 20% by weight, or no active ingredient. The weight ratio of zones with high active ingredient concentrations to zones with low active ingredient concentrations is typically in the range of from 1:10 to 10:1, in particular in the range of from 4:1 to 1:4. The difference in concentration between the zones is typically at least 0.1 g/100 g polymer, in particular at least 1 g/100 g polymer, for example 0.1 to 50 g/100 g polymer, in particular 1 to 20 g/100 g polymer.

The polymer components in the zones with high and low active ingredient concentrations, respectively, may be identical or different and preferably differ at least in the type of the monomers M1. In accordance with a first preferred embodiment of the invention, the monomers M1 which form the zones with high active ingredient concentrations are selected among $C_1$-$C_4$-alkyl methacrylates and mixtures of at least 60% by weight, in particular at least 80% by weight, of $C_1$-$C_4$-alkyl methacrylates with up to 40% by weight, in particular up to 20% by weight, of monomers M1 other than these, whereas the monomers M1 which form the zones with low active ingredient concentrations are selected among vinyl-aromatics and mixtures of at least 60% by weight, in particular at least 80% by weight, of vinyl-aromatics with up to 40% by weight, in particular up to 20% by weight, of monomers M1 which differ from these. In accordance with a second preferred embodiment of the invention, the monomers M1 which form the zones with low active ingredient concentrations are selected among $C_1$-$C_4$-alkyl methacrylates and mixtures of at least 60% by weight, in particular at least 80% by weight, of $C_1$-$C_4$-alkyl methacrylates with up to 40% by weight, in particular up to 20% by weight, of monomers M1 other than these, whereas the monomers M1 which form the zones with high active ingredient concentrations are selected among vinyl-aromatics and mixtures of at least 60% by weight, in particular at least 80% by weight, of vinyl-aromatics with up to 40% by weight, in particular up to 20% by weight, of monomers M1 which differ from these. In accordance with a third preferred embodiment of the invention, the monomers M1 which form the zones with low active ingredient concentrations are selected among $C_1$-$C_4$-alkyl methacrylates and mixtures of at least 90% by weight, of $C_1$-$C_4$-alkyl methacrylates with up to 10% by weight, of monomers M1 other than these, whereas the monomers M1 which form the zones with high active ingredient concentrations are selected among mixtures of 20 to 85% by weight, in particular 50 to 80% by weight, of $C_1$-$C_4$-alkyl methacrylates with 15 to 80% by weight, in particular 20 to 50% by weight, of monomers M1 which differ from these, in particular vinyl-aromatics. In these embodiments, methyl methacrylate is a preferred $C_1$-$C_4$-alkyl methacrylate. In these embodiments, styrene is a preferred vinyl-aromatic. It has furthermore proved advantageous when the monomers which form the zones of high active ingredient concentrations comprise the majority, in particular at least 80% by weight. In this context, all data in % by weight refer in each case to the monomers M1 which form the respective zones. Furthermore, it has proved advantageous when the monomers which form the zones of high active ingredient concentrations comprise the majority, in particular at least 80% by weight, or all of the monomers M-k employed in the polymerization. Accordingly, the percentage of the monomers M-k, based on the weight of the monomers which form the zones of high active ingredient concentrations, is preferably in the range of from 0.5 to 40% by weight, in particular in the range of from 1 to 20% by weight. It has furthermore proved advantageous when the monomers which form the zones of low active ingredient concentrations comprise at least one crosslinking monomer, for example a monomer M2c. Accordingly, the percentage of the monomers M2c, based on the weight of the monomers which form the zones of low active ingredient concentrations, is preferably in the range of from 0.01 to 4% by weight, in particular in the range of from 0.05 to 2% by weight.

The compositions according to the invention comprise one or more insecticidal active ingredients with a low solubility in water of, as a rule, not more than 5 g/l, preferably not more than 3 g/l and in particular not more than 1 g/l, for example 0.001 to 1 g/l or 0.002 to 0.5 g/l at 25° C. at 1013 mbar. Typically, they take the form of organic substances, in particular of compounds with a defined composition, i.e. a defined empirical formula, or mixtures of compounds with a defined composition. As a rule, they take the form of low-molecular-weight substances with a molecular weight of not more than 500 daltons. Typically, the insecticidal active ingredients are soluble up to the polymerization temperature in the monomers M in at least the amount employed. As a rule, a solubility in monomers M of 1 g/l at 25° C. at 1013 mbar is advantageous. Examples of suitable insecticidal ingredients are the compounds listed in the Compendium of Pesticide Common Names (Index of common names) as insecticides. These include, for example:

organo(thio)phosphates such as acephate, azamethiphos, azinphos-methyl, chlorpyrifos, chlorpyriphos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, terbufos, triazophos, trichlorfon;

carbamates such as alanycarb, benfuracarb, bendiocarb, carbaryl, carbosulfan, fenoxycarb, furathiocarb, indoxacarb, methiocarb, methomyl, oxamyl, pirimicarb, propoxur, thiodicarb, triazamate;

pyrethroids such as allethrin, bifenthrin, cyfluthrin, cyphenothrin, cypenmethrin and the alpha, beta, theta und zeta isomers, deltamethrin, esfenvalerate, ethofenprox, fenpropathrin, fenvalerate, cyhalothrin, lambda-cyhalothrin, imiprothrin, permethrin, prallethrin, pyrethrin I, pyrethrin II, silafluofen, tau-fluvalinate, tefluthrin, tetramethrin, tralomethrin, transfluthrin, zeta-cypermethrin;

arthropod growth regulators such as a) chitinsynthesis inhibitors; for example benzoylureas such as chlorfluazuron, cyromacin, diflubenzuron, flucycloxuron, flufenoxuron, hexaflumuron, lufenuron, novaluron, teflubenzuron, triflumuron; buprofezin, diofenolan, hexythiazox, etoxazole, clofentazin; b) ecdysone antagonists such as halofenozide, methoxyfenozide, tebufenozide; c) juvenoids such as pyriproxyfen, methoprene, fenoxycarb; d) lipidbiosynthesis inhibitors such as spirodiclofen, spiromesifen and spirotetramate;

neonicotinoids such as flonicamid, clothianidin, dinotefuran, imidacloprid, thiamethoxam, nitenpyram, nithiazin, acetamiprid, thiacloprid;

pyrazole insecticides (GABA antagonists) such as acetoprole, ethiprole, fipronil, pyriprole, pyrafluprole, tebufenpyrad, tolfenpyrad and vaniliprole.

Furthermore abamectin, acequinocyl, amidrazone, amidoflumat, amitraz, azadirachtin, bifenazate, cartap, chlorfenapyr, chlordimeform, cyromazine, diafenthiuron, diofenolan, emamectin, endosulfan, fenazaquin, formetanate, formetanate-hydrochloride, hydramethylnon, indoxacarb, metaflumizon (=4-{(2Z)-2-({[4-(trifluoromethoxy)anilino]carbonyl}hydrazono)-2-[3-(trifluoromethyl)phenyl]ethyl}benzonitrile), pyridaben, pymetrozine, spinosad, tebufenpyrad, flupyrazaphos, flonicamid, flufenerim, flubendiamide, bistrifluoron, NC512, benclothiaz, cyflumethofen, milbermectin, cyclometofen, lepimectin, profluthrin, dimefluthrin, N-ethyl-2,2-cichloro-1-methylcyclopropanecarboxamide-2-(2,6-dichloro-α,α,α-trifluoro-p-tolyl)hydrazone, N-ethyl-2,2-dimethylpropionamide-2-(2,6-dichloro-4-trifluoromethylphenyl)hydrazone, thiocyclam, pyridalyl and the compound of the formula.

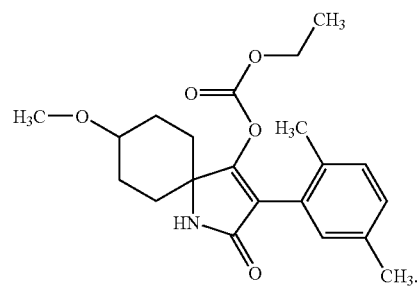 [SMILES: CCOC(=O)OC1=C(c2cc(C)ccc2C)C(=O)NC12CCC(OC)CC2]

described in WO 98/05638.

Preferred among these are insecticides which are effective against wood-destroying insects, in particular against wood-destroying beetles, termites (*Isoptera*) and ants (Formicidae), and in particular against the following wood-destroying insects:

Order Coleoptera (beetles):
Cerambycidae, such as *Hylotrupes bajulus, Callidium violaceum;*
Lyctidae, such as *Lyctus linearis, Lyctus brunneus;*
Bostrichidae, such as *Dinoderus minutus;*
Anobiidae, such as *Anobium punctatum, Xestobium nufovillosum;*
Lymexylidae, such as *Lymexylon navale;*

Platypodidae, such as *Platypus cylindrus*;
Oedemeridae, such as *Nacerda melanura*.
Order *Hymenoptera*(hymenopterons):
Formicidae, such as *Camponotus abdominalis, Lasius flavus, Lasius brunneus, Lasius fuliginosus*;
Order *Isoptera*(termites):
Calotermitidae, such as *Calotermes flavicollis, Cryptothermes brevis*;
Hodotermitidae, such as *Zootermopsis angusticollis, Zootermopsis nevadensis*;
Rhinotermitidae, such as *Reticulitermes flavipes, Reticulitermes lucifugus, Coptotermes formosanus, Coptotermes acinaciformis*;
Mastotermitidae wie *Mastotermes darwiniensis*.

They include, in particular, the insecticidal active ingredients from the classes of the pyrethroids, carbamates, organo(thio)phosphates, arthropod growth regulators such as chitin biosynthesis inhibitors, ecdysone antagonists, juvenoids, lipid biosynthesis inhibitors, neonicotinoids, pyrazole insecticides and chlorfenapyr.

Especially preferred are those insecticidal active ingredients mentioned in the Biocidal Products Directive of the European Union (COMMISSION REGULATION (EC) No. 2032/2003 of Nov. 4, 2003) in class 08 (timber preservatives) and 18 (insecticides, acaricides and substances for controlling other arthropods).

The insecticidal active ingredient is usually present in the active ingredient composition according to the invention in an amount of from 0.1 to 50% by weight, preferably in an amount of from 0.2 to 30% by weight and in particular in an amount of from 0.5 to 20% by weight, based on the monomers M which form the polymer.

In principle, the polymer particles comprised in the compositions according to the invention may comprise further active ingredients, in addition to the at least one insecticidal active ingredient. In particular, the polymer particles comprise the insecticidal active ingredient as the sole active ingredient. In one embodiment of the invention, the amount of fungicidal active ingredients is <1% by weight based on the insecticidal active ingredient comprised in the polymer particles, or <0.1% by weight based on the total amount of polymer and active ingredient.

The total amount of active ingredient in the polymer of the compositions according to the invention preferably accounts for 0.2 to 50% by weight, in particular 0.5 to 30% by weight and especially preferably 1 to 20% by weight, based on the polymer, or on the monomers M which form the polymer.

To stabilize the polymer particles in the aqueous medium, the aqueous compositions according to the invention usually comprise surface-active substances. These include not only protective colloids, but also low-molecular-weight emulsifiers, the latter, in contrast to the protective colloids, generally having a molecular weight of less than 2000 g/mol, in particular less than 1000 g/mol (mass average). The protective colloids and emulsifiers can be either of the cationic, anionic, neutral or else zwitterionic type.

The cationic surface-active substances can take the form of cationic emulsifiers, but also of cationic protective colloids, which differ from the emulsifiers mainly by a higher molecular weight which, as a rule, is at least 1000 daltons and in particular in the range of 1000 to 50 000 daltons (number average).

The cationic emulsifiers typically take the form of compounds which have at least one long-chain hydrocarbon radical with typically 6 to 30 C atoms, in particular 8 to 22 C atoms, and at least one protonated or in particular quaternized nitrogen atom, for example in the form of an ammonium, pyridinium or imidazolium group. Besides, the cationic emulsifiers may also have oligo ether groups, in particular oligoethylene oxide groups (degree of ethoxylation typically 2 to 40).

Examples of cationic emulsifiers comprise quaternary ammonium salts, for example trimethyl- and triethyl-$C_6$-$C_{30}$-alkylammonium salts such as cocotrimethylammonium salts, trimethylcetylammonium salts, dimethyl- and diethyl-di-$C_4$-$C_{20}$-alkylammonium salts such as didecyldimethylammonium salts and dicocodimethylammonium salts, methyl- and ethyl-tri-$C_4$-$C_{20}$-alkylammonium salts such as methyltrioctylammonium salts, $C_1$-$C_{20}$-alkyl-di-$C_1$-$C_4$-alkylbenzylammonium salts such as triethylbenzylammonium salts and cocobenzyldimethylammonium salts, ethoxylated and quaternized $C_6$-$C_{30}$-alkylamines (degree of ethoxylation typically 2 to 49), for example quaternization products of ethoxylated oleylamine with a degree of ethoxylation of 2 to 20, in particular 4 to 8, methyl- and ethyl-di-$C_4$-$C_{20}$-alkyl-poly(oxyethyl)ammonium salts, for example didecylmethylpoly(oxyethyl)ammonium salts, N—$C_6$-$C_{20}$-alkylpyridinium salts, for example N-laurylpyridinium salts, N-methyl- and N-ethyl-N—$C_6$-$C_{20}$-alkylmorpholinium salts, and N-methyl- and N-ethyl-N'—$C_6$-$C_{20}$-alkylimidazolinium salts, in particular the halides, borates, carbonates, formates, acetates, propionates, hydrogencarbonates, sulfates and methylsulfates.

The cationic protective colloids typically take the form of homo- and copolymers of ethylenically unsaturated monomers which comprise incorporated into the polymer at least one of the abovementioned monomers M-k in an amount of at least 20% by weight, in particular at least 30% by weight, based on the total weight of the monomers which constitute the cationic protective colloid. In addition, the protective colloids may comprise incorporated into the polymer neutral comonomers. In the copolymers which are suitable as protective colloids, the amount of neutral comonomers typically accounts for 5 to 80% by weight, in particular 10 to 70% by weight, based on the total amount of the monomers which constitute the cationic protective colloids. Suitable comonomers are, in particular, neutral monoethylenically unsaturated monomers which are miscible with water. These include N-vinyl lactams, for example N-vinylpyrrolidone, N-vinyl caprolactam, N-vinylamides of aliphatic $C_1$-$C_{10}$-carboxylic acids, such as N-vinylformamide, N-vinylacetamide, N-vinylpropionamide, N-vinyl-M-methylacteamide and the like, amides of monoethylenically unsaturated monocarboxylic acids having, as a rule, 3 to 5 C atoms, such as acrylamide, methacrylamide, hydroxyalkyl esters of monoethylenically unsaturated monocarboxylic acids having, as a rule, 3 to 5 C atoms, for example esters of acrylic acid or of methacrylic acid, such as hydroxyethyl acrylate, hydroxyethyl methacrylate, hydroxypropyl acrylate, hydroxypropyl methacrylate, hydroxybutyl acrylate and hydroxybutyl methacrylate, furthermore esters of monoethylenically unsaturated monocarboxylic acids having, as a rule, 3 to 5 C atoms, for example esters of acrylic acid or of methacrylic acid with oligoethylene oxide or monoalkyl oligoethylene oxide. Besides the water-miscible neutral monomers, suitable comonomers are also monoethylenically unsaturated comonomers which are not miscible with water. These include, in particular, vinylaromatic monomers such as styrene, α-methylstyrene, tert-butylstyrene and vinyltoluene, esters of α,β-monoethylenically unsaturated mono- and dicarboxylic acids having 3 to 8 and in particular 3 or 4 C atoms with $C_1$-$C_{10}$-alkanols or with $C_5$-$C_8$-cycloalkanols, in particular the esters of acrylic acid, of methacrylic acid, of crotonic acid, the diesters of maleic acid, of fumaric acid and of itaconic acid, and especially preferably the esters of acrylic acid with $C_2$-$C_{10}$-alkanols (=$C_2$-$C_{10}$-alkyl acrylates), such as ethyl acrylate, n-butyl acrylate, isobutyl acrylate, tert-butyl acrylate, n-hexyl acrylate, 2-ethylhexyl acrylate and 3-propylheptyl acrylate, and the esters of methacrylic acid with $C_2$-$C_{10}$-alkanols such as ethyl methacrylate, n-butyl methacrylate, isobutyl methacrylate, tert-butylmethacrylate, n-hexyl methacrylate and the like; vinyl and allyl esters of aliphatic carboxylic acids having 3 to 10 C atoms, for example vinyl propionate, and the vinyl esters of the Versatic® acids (vinyl versatates), conjugated diolefins such as butadiene and isoprene, and $C_2$-$C_{12}$-olefins such as ethylene, propene, 1-butene, n-hexene and diisobutene.

Preferred protective colloids are
homopolymers of N-vinyl-N-methylimidazolinium salts or of N-alkylvinylpyridinium salts or of monomers of the formula I, copolymers of these monomers
copolymers of N-vinyl-N-methylimidazolinium salts, of N-alkylvinylpyridinium salts or of monomers of the formula I with the abovementioned water-miscible comonomers, where the amount of the water-miscible comonomers typically accounts for 5 to 80% by weight, in particular 10 to 70% by weight, based on the total amount of the monomers which constitute the cationic protective colloid, and
copolymers which are constructed of 30 to 95% by weight, in particular 50 to 90% by weight, of at least one monomer M-k selected from among N-vinyl-N-methylimidazolinium salts, N-alkylvinylpyridinium salts and monomers of the formula I, and of at least one comonomer which is not miscible with water, the amount of such comonomers typically account for 5 to 70% by weight, in particular 10 to 50% by weight, based on the total amount of the monomers which constitute the cationic protective colloids,
terpolymers which are constructed of 20 to 90% by weight, in particular 30 to 90% by weight, of at least one monomer M-k selected from among N-vinyl-N-methylimidazolinium salts, N-alkylvinylpyridinium salts and monomers of the formula I, 5 to 60%, in particular 5 to 40% by weight, of at least one comonomer which is not miscible with water, and 5 to 75% by weight, in particular 5 to 65% by weight, of at least one comonomer which is miscible with water.

Such protective colloids are known and commercially available, for example under the trade names Luviquat and Sokalan (BASF Aktiengesellschaft).

Cationic protective colloids which are furthermore suitable are polyethyleneimines and their quaternization products, and polyvinylamines which are obtainable by hydrolyzing homo- and copolymers of N-vinylformamide, and their quaternization products. Such protective colloids are likewise known and commercially available, for example under the trade names Lupasol, Hydragen and Sokalan (BASF Aktiengesellschaft).

Examples of anionic surface-active substances are anionic emulsifiers such as alkylphenylsulfonates, phenylsulfonates, alkyl sulfates, alkylsulfonates, alkyl ether sulfates, alkylphenol ether sulfates, alkyl polyglycol ether phosphates, alkyl diphenyl ethersulfonates, polyaryl phenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, including their alkali metal, alkaline earth metal, ammonium and amine salts.

Examples of anionic protective colloids are ligninsulfonic acids, condensates of sulfonated naphthalenes with formaldehyde or with formaldehyde and phenol and, if appropriate, urea, and condensates of phenylsulfonic acid, formaldehyde and urea, lignin-sulfite waste liquor and ligninsulfonates, and polycarboxylates such as polyacrylates, maleic anhydride/olefin copolymers (for example Sokalan® CP9, BASF), and alkali metal, alkaline earth metal, ammonium and amine salts of the abovementioned protective colloids.

Examples of nonionic emulsifiers are alkylphenol alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkyl polyglycosides and glycerol fatty acid esters.

Examples of nonionic protective colloids are polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers, and their mixtures.

In a preferred embodiment of the invention, the composition according to the invention comprises at least one cationic surface-active substance, in particular a cationic emulsifier.

In another preferred embodiment of the invention, the composition according to the invention comprises at least one cationic surface-active substance, in particular a cationic emulsifier, and at least one nonionic surface-active substance.

The total amount of surface-active substance is usually in the range of from 0.2 to 30% by weight, in particular in the range of from 0.3 to 20% by weight, and especially preferably 0.5 to 10% by weight, based on the monomers M. If desired, the cationic surface-active substances O-k are typically employed in amounts of from 0.2 to 12% by weight, in particular in amounts of from 0.5 to 8% by weight, based on the total amount of the monomers M to be polymerized. In the case of cationic emulsifiers, these typically are 0.5 to 12% by weight, and cationic protective colloids are 0.1 to 6% by weight, in each case based on the total amount of the monomers M. If desired, the amount of nonionic surface-active substance is preferably in the range of from 0.2 to 12% by weight, in particular 0.5 to 10% by weight, based on the total amount of monomers M which constitute the polymer.

The preparation of the aqueous compositions according to the invention comprises a radical aqueous emulsion polymerization of a monomer composition of ethylenically unsaturated monomers M, wherein the ethylenically unsaturated monomers M comprise the at least one insecticidal active ingredient in dissolved form. During the radical aqueous emulsion polymerization, the monomers are polymerized in the form of an oil-in-water emulsion of the monomers M, where the monomer droplets of the emulsion comprise the at least one insecticidal active ingredient. Here, the polymerization is carried out analogously to a conventional emulsion polymerization, with the difference that the monomer emulsion to be polymerized comprises the insecticidal active ingredient dissolved in the monomer droplets.

The oil-in-water emulsion of the active ingredient/monomer solution can be generated in situ by addition of a solution of the active ingredient in the monomers M to be polymerized into the polymerization vessel, which is under polymerization conditions. Preferably, however, the active ingredient will be dissolved in the monomers M and the resulting monomer solution will be converted into an aqueous monomer emulsion before the resulting monomer/active ingredient emulsion is subjected to polymerization reaction.

Suitable surface-active substances are the emulsifiers and protective colloids which are conventionally employed for the emulsion polymerization and which have already been mentioned above as components of the active ingredient formulations according to the invention. The amounts of surface-active substances conventionally employed for an emulsion polymerization are conventionally in the above-stated ranges, so that the total amount or part of the surface-active substances comprised in the compositions according to the invention is provided via the emulsion polymerization. However, it is also possible to employ only part, for example 10 to 90% by weight, in particular 20 to 80% by weight, of the surface-active substances comprised in the composition according to the invention in the emulsion polymerization and to add, to the emulsion polymerization, the remainder of surface-active substance after the emulsion polymerization, before or after any deodorization which has to be carried out if appropriate (after-saponification).

To ensure a cationic surface charge, it has proved useful to carry out the emulsion polymerization of the monomers M in the presence of a cationic surface-active substance. Accordingly, in a preferred embodiment of the invention, the active ingredient composition according to the invention is prepared by subjecting the monomer composition to radical aqueous emulsion polymerization in the presence of a cationic surface-active substance, in particular in the presence of a cationic emulsifier. The cationic surface-active substance is employed in the emulsion polymerization in particular when the monomers M comprise no monomer M-k. However, it has also proved useful to carry out the emulsion polymerization in the presence of a cationic surface-active substance O-k even when the monomers M do comprise a monomer M-k.

If desired, the cationic surface-active substances O-k are typically employed in amounts of from 0.2 to 12% by weight, in particular in amounts of from 0.5 to 8% by weight, based on the total amount of the monomers M to be polymerized. In the case of cationic emulsifiers, the amount is typically 0.5 to 12% by weight, in the case of cationic protective colloids 0.1 to 6% by weight, in each case based on the total amount of the monomers M.

If appropriate, it may be advantageous to carry out the emulsion polymerization in the presence of at least one nonionic surface-active substance, in particular in combination with a cationic surface-active substance. Nonionic surface-active substances which are suitable are the nonionic surface-active compounds mentioned hereinabove.

The amount of nonionic surface-active substance which is employed in the emulsion polymerization is typically in the range of from 0.1 to 20% by weight, in particular in the range of from 0.2 to 17% by weight, based on the total amount of the monomers M to be polymerized.

The total amount of surface-active substance which is employed in the emulsion polymerization is typically in the range of from 0.2 to 30% by weight, in particular in the range of from 0.5 to 20% by weight, based on the total amount of the monomers M to be polymerized.

As a rule, the polymerization reaction is carried out by what is known as a monomer feed method, i.e. the bulk, preferably at least 70% and in particular at least 90% of the solution of the active ingredient in the monomers M, or the bulk, preferably at least 70% and in particular at least 90% of the monomer/active ingredient emulsion, is run into the polymerization vessel in the course of the polymerization reaction. Preferably, the monomer/active ingredient solution or emulsion is added over a period of at least 0.5 hour, preferably at least 1 hour, for example 1 to 10 hours and in particular 2 to 5 hours. The monomer/active ingredient solution or emulsion can be added at a constant or variable addition rate, for example in intervals with a constant addition rate or with a variable addition rate or continuously with a variable addition rate. During the addition, the composition of the monomer/active ingredient solution or emulsion may remain constant or be changed, it being possible to carry out changes both with regard to the monomer composition and with regard to the nature of the active ingredient or the concentration of the active ingredient.

In a preferred embodiment of the invention, the monomer composition is altered during the course of the monomer addition in such a way that polymer zones with different glass transition temperatures are obtained in the polymer particles. This is achieved by what is known as step-growth polymerization. To this end, a first monomer/active ingredient solution or emulsion whose monomer composition corresponds to a glass transition temperature $T_G^1$ is initially polymerized in a first step, and to this there is subsequently added a second monomer/active ingredient solution or emulsion whose monomer composition corresponds to a glass transition temperature $T_G^2$ (step 2) followed, if appropriate, by successive addition of one or more further monomer/active ingredient solutions or emulsions whose monomer composition corresponds in each case to a glass transition temperature $T_G^n$, where n stands for the step in question. Preferably, the respective glass transition temperatures in polymers obtained in successive polymerization steps differ by at least 10 K, in particular by at least 20 K and especially preferably by at least 30 K, for example 30K to 200 K, in particular 40 K to 160 K. As a rule, the amount of monomer polymerized in an amount of monomer will amount to at least 5% by weight, preferably to at least 10% by weight, for example to 5 to 95% by weight, in particular to 10 to 90% by weight, in the case of a 2-step polymerization, and to 5 to 90%, or 5 to 85% by weight, in particular to 10 to 80% by weight, in the case of a three- or multi-step polymerization.

The preparation of the aqueous active ingredient compositions according to the invention in which the polymer particles have zones with high active ingredient concentrations and zones with low active ingredient concentrations may be accomplished in analogy to the preparation of known multiphase emulsion polymers by a multi-step emulsion polymerization method, with the difference that the monomers which form the zones which are high in active ingredient (monomers $M_a$) have a higher active ingredient concentration than the monomers which form the zones with lower active ingredient concentrations (monomers $M_b$). Typically, the monomers $M_a$ comprise at least 70% by weight and preferably at least 80% by weight or the total amount of the insecticidal active ingredient present in the composition in dissolved form. Accordingly, the monomers $M_b$ comprise the remainder of insecticidal active ingredient, i.e. no more than 30% by weight, in particular no more than 20% by weight, or no insecticidal active ingredient.

Multi-phase emulsion polymers and processes for their preparation are known in principle from the prior art, for example from "Emulsions Polymerization and Emulsion Polymers" (M. S. El-Asser et al., Editor), Wiley, Chichester 1997, Chapter 9, p. 293-326 and references cited therein; Y. C. Chen et al, J. Appl. Polym. Sci. 41 (1991), p. 1049; I. Cho et al. J. Appl. Polym. Sci. 30 (1985), p. 1903; D. R. Stuterman et al, Ind, Eng. Prod. Res. Dev. 23 (1985), p. 404; S. Lee et al., Polym. Chem. 30 (1992), p. 2211; Y. C. Chen et al., Macromolecules 24 (1991) 3779, C. L. Winzor et al., Polymer 18 (1992) p. 3797. As a rule, they are prepared by sequential emulsion polymerization of at least one first monomer emulsion which forms a first monomer phase, and at least one second monomer emulsion which forms at least one further polymer phase, it being possible to control the morphology of the polymer particles, and hence also the relative arrangement of the polymer phases in the polymer particles, via the sequence in which the monomer emulsions are polymerized, but also via the monomer composition and the polymerization conditions.

The sequence of the polymerization of the monomers $M_a$ and $M_b$ is of minor importance since phase separation into an external and an internal phase frequently depends in a manner known per se on the relative monomer composition and not on the sequence of the polymerization. However, a procedure will frequently be followed in which the monomers $M_b$ are first polymerized and the monomers $M_a$ afterwards, in order to obtain polymer particles with external zones with high active ingredient concentrations and internal zones with low active ingredient concentrations.

As a rule, the polymerization of the monomers $M_a$ and $M_b$ is carried out by what is known as a monomer feed process, i.e. the majority, preferably at least 70% and in particular at least 90% of the solution of the active ingredient in the monomers $M_a$, or the majority, preferably at least 70% and in particular at least 90% of the monomer/active-ingredient emulsion is fed into the polymerization vessel in the course of the polymerization reaction. The addition of the monomer/active ingredient solution or emulsion is preferably accomplished over a period of at least 0.5 h, preferably at least 1 h, for example, 1 to 10 h and in particular 2 to 5 h. The addition of the monomer/active ingredient solution or emulsion can be accomplished at a constant or variable feed rate, for example in intervals with a constant feed rate or with a variable feed rate or continuously with a variable feed rate. The composition of the monomer/active ingredient solution or emulsion can remain constant during the addition or may be modified, it being possible to carry out modifications both regarding the monomer composition and regarding the nature of the active ingredient or the concentration of the active ingredient.

It has proved advantageous for the preparation of the active ingredient composition according to the invention and for the characteristics of the active ingredient composition to carry out the emulsion polymerization in the presence of a seed polymer (seed latex). These take the form of a finely divided polymer latex whose mean particle size is usually not greater than 100 nm, in particular not greater than 80 nm and especially preferably not greater than 50 nm. The monomers which constitute the seed latex are preferably selected to at least 90% by weight, in particular at least 95% by weight and frequently more than 99% by weight among the monomers M1, it also being possible for the seed latex to comprise small amounts, for example from 0.1 to 10% by weight, in particular from 0.1 to 5% by weight and specifically from 0.1 to 1% by weight of different, M2, monomers, for example monomers M2a, for stabilization purposes. Frequently, the seed latex has a glass transition temperature of at least 10, in particular at least 50 and frequently at least 80° C. The amount of seed latex is usually from 0.01 to 5% by weight, in particular from 0.1 to 4% by weight, based on the amount of monomers M1 to be polymerized. Preferably, all of the bulk, and in particular of the entirety, of the seed latex is in the reaction vessel at the beginning of the polymerization reaction. The seed latex can also be generated in situ in the polymerization vessel by radical emulsion polymerization of the monomers which form the seed latex, the monomers which form the seed latex being selected among the abovementioned monomers M1 and M2 and in particular to at least 90% by weight among the monomers M1. The desired particle size of the seed latex can be controlled in the manner known per se via the monomer/emulsifier ratio.

The starters which are suitable for the emulsion polymerization according to the invention are the conventionally used polymerization initiators which are suitable for an emulsion polymerization and which trigger a radical polymerization of the monomers M. These include azo compounds such as 2,2'-azobis-isobutyronitrile, 2,2'-azobis-(2-methylbutyronitrile), 2,2'-azobis[2-methyl-N-(–2-hydroxyethyl)propionamide, 1,1'-azobis(1-cyclohexanecarbonitrile), 2,2'-azobis(2,4-dimethylvaleronitrile), 2,2'-azobis(N,N'-dimethyleneisobutyroamidine) dihydrochloride, and 2,2'-azobis(2-amidinopropane) dihydrochloride, organic or inorganic peroxides such as diacetyl peroxide, di-tert-butyl peroxide, diamyl peroxide, dioctanoyl peroxide, didecanoyl peroxide, dilauroyl peroxide, dibenzoyl peroxide, bis(o-tolyl) peroxide, succinyl peroxide, tert-butyl peracetate, tert-butyl permaleate, tert-butyl perisobutyrate, tert-butyl perpivalate, tert-butyl peroctoate, tert-butyl perneodecanoate, tert-butyl perbenzoate, tert-butyl peroxide, tert-butyl hydroperoxide, cumene hydroperoxide, tert-butyl peroxy-2-ethylhexanoate and diisopropyl peroxydicarbamate; salts of peroxodisulfuric acid and redox initiator systems.

It is preferred to employ water-soluble initiators, for example cationic azo compounds such as azobis(dimethylamidinopropane), salts of peroxodisulfuric acid, in particular sodium, potassium or ammonium salts, or a redox initiator system which comprises, as oxidant, a salt of peroxodisulfuric acid, hydrogen peroxide or an organic peroxide such as tert-butyl hydroperoxide. As reducing agent, they preferably comprise a sulfur compound which is selected in particular from among sodium hydrogen sulfite, sodium hydroxymethanesulfinate and the hydrogen sulfite adduct with acetone. Further suitable reducing agents are phosphorus-comprising compounds such as phosphorous acid, hypophosphites and phosphinates, and also hydrazine or hydrazine hydrate, and ascorbic acid. Furthermore, redox initiator systems may comprise an addition of small amounts of redox metal salts such as iron salts, vanadium salts, copper salts, chromium salts or manganese salts, such as, for example, the redox initiator system ascorbic acid/iron(II) sulfate/sodium peroxodisulfate.

Usually, the initiator is employed in an amount of from 0.02 to 2% by weight and in particular from 0.05 to 1.5% by weight, based on the amount of the monomers M. The optimal amount of the initiator will naturally depend on the initiator system employed and can be determined by the skilled worker in routine experiments. The reaction vessel can initially be charged with some or all of the initiator. Preferably, the bulk of the initiator, in particular at least 80%, for example 80 to 99.5% of the initiator, is added to the polymerization reactor in the course of the polymerization reaction.

Pressure and temperature are of minor importance for the preparation of the active ingredient compositions according to the invention. The temperature will naturally depend on the initiator system employed, and an optimal polymerization temperature can be determined by the skilled worker by routine experimentation. The polymerization temperature is usually in the range of from 20 to 110° C., frequently in the range of from 50 to 95° C. The polymerization reaction is usually carried out under atmospheric pressure or ambient pressure. However, it can also be carried out under elevated pressure, for example at up to 3 bar or at slightly reduced pressure, for example >800 mbar.

Naturally, the molecular weight of the polymers can be adjusted by addition of a small amount of regulators, for example 0.01 to 2% by weight, based on the monomers M to be polymerized. Suitable regulators are, in particular, organic thiol compounds, further allyl alcohols and aldehydes.

After the actual polymerization reaction, if appropriate it is necessary to make the aqueous polymer dispersions according to the invention largely free from odoriferous substances such as residual monomers and other organic volatile components. This can be achieved in the manner known per se by physical means by removal via distillation (in particular via steam distillation) or by stripping with an inert gas. Furthermore, the depletion of the residual monomers can be carried out chemically by radical afterpolymerization, in particular employing redox initiator systems as they are listed for example in DE-A 44 35 423, DE-A 44 19 518 and in DE-A 44 35 422. The afterpolymerization is preferably carried out with a redox initiator system consisting of at least one organic peroxide and an organic sulfite.

After the polymerization has ended, the polymer dispersions obtained can be brought to the desired pH by addition of acids or bases before they are used in accordance with the invention.

This gives stable aqueous polymer dispersions which comprise at least one insecticidal active ingredient in the polymer particles of the dispersion. In addition, the resulting dispersions comprise the abovementioned surface-active substances. The resulting active ingredient preparations are distinguished by high stability and a low content in volatile organic compounds, which usually account for not more than 1% by weight, frequently not more than 0.1% by weight and in particular not more than 500 ppm, based on the total weight of the composition. Here and hereinbelow, volatile components are all organic compounds which have a boiling point of below 200° C. under atmospheric pressure.

In a first approximation, the solids content of the compositions according to the invention is determined by the active ingredient and the polymer; it is, as a rule, in the range of from 10 to 60% by weight and in particular in the range of from 20 to 50% by weight.

The active ingredient compositions which can thus be obtained can be employed as such or directly after dilution. Moreover, the compositions according to the invention may additionally also comprise additives, for example viscosity-modifying additives (thickeners), antifoam agents, bactericides and antifreeze agents.

Suitable thickeners are compounds which confer a pseudoplastic flow behavior on the formulation, i.e. high viscosity at rest and low viscosity in the agitated state. Mention may be made, in this connection, for example, of polysaccharides such as Xanthan Gum® (Keizan® from Kelco), Rhodopol® 23 (Rhone-Poulenc) or Veegum® (R.T. Vanderbilt), and also layered minerals, organically modified if appropriate, such as Attaclay® (Engelhardt), with polysaccharides such as Xanthan Gum® preferably being used.

Antifoam agents which are suitable for the dispersions according to the invention are, for example, silicone emulsions (such as, for example, Silikon® SRE, from Wacker, or Rhodorsil® from Rhodia), long-chain alcohols, fatty acids, organofluor compounds and mixtures of these.

Bactericides can be added to stabilize the compositions according to the invention from infection by microorganisms. Suitable bactericides are, for example, Proxel® from Avecia (or Arch) or Acticide® RS from Thor Chemie and Kathon® MK from Röhm & Haas.

Suitable antifreeze agents are organic polyols, e.g. ethylene glycol, propylene glycol or glycerol. These are generally used in amounts of not more than 10% by weight, based on the total weight of the active substance composition.

If appropriate, the active substance compositions according to the invention can, to regulate the pH, comprise 1 to 5% by weight of buffer, based on the total amounts of the formulation prepared, the amounts and the type of the buffer used depending on the chemical properties of the active substance or substances. Examples of buffers for regulating the pH are alkali metal salts of weak inorganic or organic acids, such as, e.g., phosphoric acid, boric acid, acetic acid, propionic acid, citric acid, fumaric acid, tartaric acid, oxalic acid and succinic acid.

In addition, the aqueous compositions according to the invention can be formulated with conventional binders, for example aqueous polymer dispersions or water-soluble resins, for example water-soluble alkyd resins, or with waxes.

For use in the protection of lignocellulosic materials, in particular in wood preservation, the aqueous active substance compositions according to the invention can also be formulated with conventional water-soluble wood preservatives, in particular with their aqueous solutions or suspensions, in order to improve the overall effectiveness against wood-destroying organisms. In this connection, these are, for example, aqueous preparations of conventional wood-protecting salts, for example of salts based on boric acid and alkali metal borates, salts based on quaternary ammonium compounds, e.g. trimethyl- and triethyl($C_6$-$C_{30}$-alkyl)ammonium salts, such as cocotrimethylammonium chloride or trimethylcetylammonium salts, dimethyl- and diethyldi($C_4$-$C_{20}$-alkyl)ammonium salts, such as didecyldimethylammonium chloride, didecyldimethylammonium bromide or dicocodimethylammonium chloride, ($C_1$-$C_{20}$-alkyl)di($C_1$-$C_4$-alkyl)benzylammonium salts, such as cocobenzyldimethylammonium chloride, or methyl- and ethyldi($C_4$-$C_{20}$-alkyl)poly(oxyethyl)ammonium salts, e.g. didecylmethylpoly(oxyethyl)ammonium chloride and propionate, and also the borates, carbonates, formates, acetates, hydrogencarbonates, sulfates and methyl sulfates, or aqueous preparations of copper-amine complexes, in particular aqueous preparations of salts comprising copper ethanolamine, for example Cu-HDO. Obviously, the aqueous active substance preparations according to the invention can also be formulated with other aqueous fungicidal and insecticidal active substance compositions, for example with conventional emulsion concentrates, suspension concentrates or suspoemulsion concentrates of fungicides and insecticides.

Examples of fungicidal active ingredients which can be coformulated together with the active ingredient compositions according to the invention comprise the compounds listed as fungicides in the Compendium of Pesticide Common Names (Index of common names). These include, for example,
acylalanines, such as benalaxyl, metalaxyl, ofurace or oxadixyl;
morpholine compounds such as aldimorph, dodine, dodemorph, fenpropimorph, fenpropidin, guazatine, iminoctadine, spiroxamine or tridemorph;
anilinopyrimidines, such as pyrimethanil, mepanipyrim or cyprodinil;
antibiotics such as cycloheximide, griseofulvin, kasugamycin, natamycin, polyoxin or streptomycin;
azoles such as azaconazole, bitertanol, bromoconazole, cyproconazole, diclobutrazol, difenoconazole, dinitroconazole, epoxiconazole, fenbuconazole, fluquinconazole, flusilazole, flutriafol, ketoconazole, hexaconazole, imazalil, metconazole, myclobutanil, penconazole, propiconazole, prochloraz, prothioconazole, tebuconazole, tetraconazole, triadimefon, triadimenol, triflumizole or triticonazole;

dicarboximides, such as iprodione, myclozolin, procymidone or vinclozolin;

dithiocarbamates, such as ferbam, nabam, maneb, mancozeb, metam, metiram, propineb, polycarbamate, thiram, ziram or zineb;

heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole or triforine;

nitrophenyl derivatives, such as binapacryl, dinocap, dinobuton or nitrothal-isopropyl;

phenylpyrroles, such as fenpiclonil or fludioxonil;

strobilurins, such as dimoxystrobin, fluoxastrobin, kresoxim-methyl, metominostrobin, orysastrobin, picoxystrobin, pyraclostrobin and trifloxystrobin;

other fungicides, such as acibenzolar-S-methyl, benzoyl benzoate, dodecylguanidine hydrochloride, benthiavalicarb, carpropamid, chlorothalonil, cyflufenamid, cymoxanil, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, tolclofos-methyl, quintozene or zoxamide;

sulfenic acid derivatives, in particular sulfenamides such as captafol, captan, dichlofluanid, folpet or tolylfluanid;

cinnamamides and analogous compounds, such as dimethomorph, flumetover or flumorph.

They furthermore include:

iodine compounds such as diiodomethyl p-tolyl sulfone, 3-iodo-2-propynyl alcohol, 4-chlorophenyl-3-iodopropargyl formal, 3-bromo-2,3-diiodo-2-propenylethyl carbonate, 2,3,3-triiodoallyl alcohol, 3-bromo-2,3-diiodo-2-propenyl alcohol, 3-iodo-2-propynyl-n-butyl carbamate, 3-iodo-2-propynyl-n-hexyl carbamate, 3-iodo-2-propynylphenyl carbamate, O-1-(6-iodo-3-oxohex-5-ynyl)butyl carbamate, O-1-(6-iodo-3-oxohex-5-ynyl)phenyl carbamate, napcocide;

phenol derivatives such as tribromophenol, tetrachlorophenol, 3-methyl-4-chlorophenol, dichlorophene, o-phenylphenol, m-phenylphenol, 2-benzyl-4-chlorophenol;

isothiazolinones such as N-methylisothiazolin-3-one, 5-chloro-N-methylisothiazolin-3-one, 4,5-dichloro-N-octylisothiazolin-3-one, N-octylisothiazolin-3-one;

(benz)isothiazolinones such as 1,2-benzisothiazol-3(2H)-one, 4,5-trimethylisothiazol-3-one, 2-octyl-2H-isothiazol-3-one;

pyridines such as 1-hydroxy-2-pyridinethione (and their Na, Fe, Mn, Zn salts), tetrachloro-4-methylsulfonylpyridine;

metal soaps such as tin naphthenate, copper naphthenate, zinc naphthenate, tin octoate, copper octoate, zinc octoate, tin 2-ethylhexanoate, copper 2-ethylhexanoate, zinc 2-ethylhexanoate, tin oleate, copper oleate, zinc oleate, tin phosphate, copper phosphate, zinc phosphate, tin benzoate, copper benzoate or zinc benzoate;

organotin compounds such as, for example, tributyl(TBT) tin compounds such as tributyltin and tributyl(mononaphthenoyloxy)tin derivatives;

dialkyl dithiocarbamate and the Na and Zn salts of dialkyl dithiocarbamates, tetramethylthiuram disulfide;

nitriles such as 2,4,5,6-tertrachloroisophthalonitrile;

benzthiazoles such as 2-mercaptobenzothiazole;

quinolines such as 8-hydroxyquinoline, and their Cu salts;

tris-(N-cyclohexyldiazeniumdioxy)aluminum, (N-cyclohexyldiazeniumdioxy)tributyltin, bis(N-cyclohexyldiazeniumdioxy)copper;

3-benzo[b]thien-2-yl-5,6-dihydro-1,4,2-oxathiazine 4-oxide (bethoxazin).

With a view to the use of the compositions according to the invention for the protection of lignocellulosic materials, preferred fungicides are in particular those which are effective for example against molds, wood-discoloring and wood-destroying fungi or other wood-destroying microorganisms: examples of wood-damaging microorganisms are Wood-Discoloring Fungi:

Ascomycetes such as *Ophiostoma* sp. (e.g. *Ophiostoma piceae, Ophiostoma piliferum*), *Ceratocystis* sp. (for example *Ceratocystis coerulescens*), *Aureobasidium pullulans, Sclerophoma* sp. (for example *Sclerophoma pityophila*);

Deuteromycetes such as *Aspergillus* sp. (for example *Aspergillus niger*), *Cladosporium* sp. (for example *Cladosporium sphaerospermum*), *Penicillium* sp. (for example *Penicillium funiculosum*), *Trichoderma* sp. (for example *Trichoderma viride*), *Alternaria* sp. (for example *Alternaria alternata*), *Paecilomyces* sp. (for example *Paecilomyces variotii*);

Zygomycetes such as *Mucor* sp. (for example *Mucor hiemalis*) and

Wood-Destroying Fungi:

Ascomycetes such as *Chaetomium* sp. (for example *Chaetomium globosum*), *Humicola* sp. (for example *Humicola grisea*), *Petriella* sp. (for example *Petriella setifera*), *Trichurus* sp. (for example *Trichurus spiralis*);

Basidiomycetes such as *Coniophora* sp. (for example *Coniophora puteana*), *Coriolus* sp. (for example *Coriolus versicolor*), *Gloeophyllum* sp. (for example *Gloeophyllum trabeum*), *Lentinus* sp. (for example *Lentinus lepideus*), *Pleurotus* sp. (for example *Pleurotus ostreatus*), *Poria* sp. (for example *Poria placenta, Poria vaillantii*), *Serpula* sp. (for example *Serpula lacrymans*) and *Tyromyces* sp. (for example *Tyromyces palustris*), Fungicidal active ingredients from the group of the conazoles, the group of the morpholines, the group of the strobilurins, the group of the thiazoles, the group of the sulfenamides and the group of the iodine compounds are particularly suitable against these. Preferred are in particular those fungicides which are mentioned in the Biocidal Products Directive of the European Union (COMMISSION REGULATION (EC) No. 2032/2003 of 4 Nov. 2003) in Class 08 (timber preservatives).

The aqueous active ingredient compositions according to the invention may comprise the fungicidal active ingredient in an amount of from 0.1 to 30% by weight, preferably in an amount of from 0.2 to 25% by weight and in particular in an amount of from 0.5 to 20% by weight, based on the total weight of the composition.

By mixing the aqueous active ingredient composition according to the invention with conventional aqueous preparations of the abovementioned active substances, a broadening in the spectrum of activity is first obtained, if the conventional preparation comprises a different active ingredient from the aqueous active ingredient composition according to the invention. Secondly, the advantages of the active ingredient compositions according to the invention are not lost by formulating with conventional aqueous active ingredient preparations, in particular the improved adhesion to lignocellulosic materials and especially to wood. Consequently, the application properties of a conventional aqueous active ingredient preparation can be improved by formulating with an aqueous active ingredient composition according to the invention of the same active ingredient.

There are a number of advantages to the active ingredient compositions according to the invention. First, these are stable aqueous formulations of insecticidal active ingredient which are insoluble in water or are soluble in water only to a slight extent. In particular, the phase separation problems observed in conventional suspension formulations and in micro- or nanodispersions of the active ingredient are not observed and settling of the active ingredient is not observed, even when drastic conditions are employed, such as occur in the processes employed for impregnating wood with insecticidal active ingredients. The content of volatile organic compounds is lower with conventional additivating than with comparable conventional formulations and, in comparison to micro- or nanodispersions of active ingredients, the proportion of emulsifier is simultaneously lower, based on the active ingredient used. The active ingredient is leached from the treated material, under the effect of water, to a markedly lesser extent in comparison with other formulations. Furthermore, interactions of the active ingredients with other formulation constituents or additional active ingredients, such as frequently occur with a conventional formulation, are not observed. Furthermore, the decomposition of the active ingredients by the effects of the substrate or environment, such as pH value of the medium or UV radiation, is slowed down or even completely halted. Surprisingly, a reduced effectiveness of the active ingredient through the incorporation in a polymer matrix is not observed.

The present invention also relates to a method for protecting lignocellulosic materials, in particular timber, against attack or destruction by harmful insects, in particular by the abovementioned wood-damaging insects. The method comprises treating the lignocellulosic material with an aqueous insecticide composition according to the invention and/or with a pulverulent insecticide composition prepared therefrom.

Lignocellulosic materials are, in addition to wood and downstream products, e.g. wood blanks, plywood, chipboard, MDF panels or OSB panels, also pulps and intermediates in the manufacture of paper, fabrics based on lignocellulose, such as cotton, materials based on woody annuals, for example molded articles formed from rape shavings, bargasse panels, straw panels, and the like. The lignocellulosic materials furthermore include articles formed from lignocellulosic fiber materials, such as fabrics, formed fabrics, paper, board, heat-insulating materials, ropes, cables, and the like. Suitable fiber materials for the process according to the invention comprise textile fibers, such as flax, linen, hemp, jute, cotton and ramie, paper fibers, such as flax, linen or hemp, bamboo fibers, paper mulberry and lignocellulose fibers, and also nettle fiber, manila hemp, sisal, kenaf and coconut fiber.

The treatment can be carried out in a way known per se, depending on the type of substrate, by spraying, painting, dipping or impregnating the substrate with an undiluted active ingredient composition according to the invention or an active ingredient composition according to the invention diluted with water or by flooding the substrate in an undiluted aqueous active ingredient composition according to the invention or an aqueous active ingredient composition according to the invention diluted with water. The compositions according to the invention can also be present in the manufacture of the lignocellulosic material, for example as binder or as sizing agent.

If the substrate according to the invention is wood, use may be made of the processes conventional in wood preservation, such as are known, for example, from Ullmann's Encyclopedia of Industrial Chemistry, Wood preservation, 5th edition on CD-ROM, Wiley VCH, Weinheim, 1997, chapter 7. These include in particular processes for impregnating the wood with the help of pressure differences, e.g. the vacuum-pressure process and double vacuum impregnation.

The treatment of such materials with the active ingredient compositions according to the invention can be carried out according to the processes conventional for this and will be adapted in a way known per se to the technical realities in each case. The application concentration and the incorporation depend in this connection on the degree of danger of the material and on the respective treatment process and usually range from 0.05 mg to 10 g of active ingredient per kg of material.

The undiluted composition comprising the active ingredient is frequently used in wood downstream products and lignocellulosic materials, for example together with the binder used, as cobinder. Obviously, separate treatment during or after the manufacture, for example the sizing, is also possible.

In addition to the lignocellulose-based materials mentioned, the aqueous active ingredient composition according to the invention can also be used in other areas of material protection from infection by animal pests. For example, skin, fur or leather can be effectively protected, with the aqueous compositions according to the invention or the powders produced therefrom, from infection by animal pests.

The examples which follow are intended to illustrate, but not to limit, the invention:

EXAMPLE 1

Dispersions D1 and D2

General Preparation Protocol:
465 g of deionized water, 5% by weight of feed 1 and 10% by weight of feed 2 were heated at 80° C. After 10 minutes, adding the remainder of feeds 1 and 2 was started. The feed time was 3.5 hours. After feeding had ended, the mixture was held for a further 30 minutes at 80° C. and then cooled to room temperature.

Feed 1:
496.1 g of deionized water
7.6 g of sulfuric acid (50% by weight)
361.0 g of methyl methacrylate
19.0 g of dimethylaminoethyl methacrylate
57.0 g of emulsifier solution E1
x g of active ingredient (see Table 1)
Feed 2:
Solution of 1.5 g of 2,2-'azobis(N,N'-dimethylisobutyramidine) in 63.3 g of deionized water Emulsifier solution E1: 40% by weight strength aqueous solution of a cationic emulsifier obtained by successive ethoxylation of stearylamine with 4-5 mols of ethylene oxide, followed by quaternization with dimethyl sulfate.

TABLE 1

| Dispersion | Active ingredient | x [g] |
|---|---|---|
| D1 | Chlorfenapyr | 5 |
| D2 | α-Cypermethrin | 65 |

The resulting dispersions had a solids content of approximately 29.5% by weight and a viscosity of 100 mPa·s. The polymer had a glass transition temperature at 87° C., determined by means of DSC. The mean particle size, determined by means of light scattering, was 157 to 175 nm.

EXAMPLE 2

Dispersions D3 and D4

General Preparation Protocol:

465 g of deionized water, feed 1 and 10% by weight of feed 2 were heated at 80° C. After 10 minutes, adding the remainder of feed 2 and feed 3 was started. The feed time of feed 2 and feed was 3.5 hours. After feeding had ended, the mixture was held for a further 30 minutes at 80° C. and then cooled to room temperature.

Feed 1:
46.1 g of deionized water
38.0 g of styrene
7.6 g of 3-(N,N)-dimethylaminopropylmethacrylamide
14.2 g of emulsifier solution E1 (see above)

Feed 2:
Solution of 1.5 g of 2,2-'azobis(N,N'-dimethylisobutyramidine) in 63.3 g of deionized water Feed 3:
450.1 g of deionized water
7.6 g of acrylic acid
270.0 g of methyl methacrylate
57.0 g of dimethylaminoethyl methacrylate
42.8 g of emulsifier solution E1 (see above)
x g of active ingredient (see Table 2)

TABLE 2

| Dispersion | Active ingredient | x [g] |
|---|---|---|
| D3 | Chlorfenapyr | 61.8 |
| D4 | α-Cypermethrin | 42.9 |

The resulting dispersions had a solids content of approximately 29.8% by weight and a viscosity of 105 mPa·s. The polymer had a glass transition temperature at 110° C., determined by means of DSC. The mean particle size, determined by means of light scattering, was 155 to 175 nm.

EXAMPLE 3

Dispersion D5

226 g of deionized water, 5% by weight of feed 1 and 10% by weight of feed 2 were heated at 80° C. After 10 minutes, adding the remainder of feeds 1 and 2 was started. The feed time was 3.5 hours. After feeding had ended, the mixture was held for a further 30 minutes at 80° C. and then cooled to room temperature.

Feed 1:
140.0 g of deionised water
3.0 g of $H_2SO_4$
22.5 g of emulsifier solution E1
30.0 g of styrene
112.5 g of methyl methacrylate
7.5 g of dimethylaminoethyl methacrylate
21.71 g of alpha-cypermethrin Feed 2: 0.6 g of 2,2'-azobis(N,N'-dimethylisobutyramidine) in 25 g of water The resulting dispersion had a solids content of 28.7% by weight and a viscosity of 100 mPa·s. The polymer had a glass transition temperature at 78.3° C., determined by means of DSC. The mean particle size determined by means of light scattering was 107 nm.

REFERENCE EXAMPLE

Anionic Dispersion D6 (Not According to the Invention)

577 g of deionized water, 5% by weight of feed 1 and 10% by weight of feed 2 were heated at 80° C. After 10 minutes, adding the remainder of feeds 1 and 2 was started. The feed time was 3.5 hours. After feeding had ended, the mixture was held for a further 30 minutes at 80° C. and then cooled to room temperature.

Feed 1:
420.0 g of water
31.3 g of emulsifier E2
23.5 g of methacrylic acid
446.5 g of methyl methacrylate
14.1 g of alpha-cypermethrin Feed 2: 75.2 g of a 2.5% by weight strength solution of sodium peroxodisulfate in water Emulsifier E2: Sodium salt of the sulfuric monoester of an ethoxylated $C_{12-14}$-alkanol (degree of ethoxylation: 30)

The resulting dispersion had a solids content of 29.8% by weight and a viscosity of 100 mPa·s. The polymer had a glass transition temperature at 122.7° C., determined by means of DSC. The mean particle size, determined by light scattering, was 178 nm.

EXAMPLE 4

Dispersions D7 to D16

Aqueous polymer dispersions D7 to D16 were prepared analogously to Example 2, the monomer compositions of feed 1 and feed 3 being indicated in Table 3. The weight ratio of the monomers in feed 1 to the monomers in feed 3 was 4:6 in all cases. In all cases, feed 3 comprised 9 pphm α-cypermethrin, based on the monomers present in feed 3. In dispersion D9, feed 1 additionally comprised 5 pphm of α-cypermethrin based on the monomers present in feed 1.

TABLE 3

|  | D7 | D8 | D9 | D10 | D11 | D12 | D13 | D14 | D15 | D16 |
|---|---|---|---|---|---|---|---|---|---|---|
| Feed 1 | | | | | | | | | | |
| Styrene pphm[1] | 78 | 100 | 99.8 | 100 | 99.8 | — | — | — | 77.8 | 77.8 |
| MMA pphm[1] | 22 | — | — | — | — | 100 | 99.8 | 99.9 | 22 | 22 |
| BDGA pphm[1] | — | — | — | — | — | — | — | — | 0.2 | — |
| AMA pphm[1] | — | — | 0.2 | — | 0.2 | — | 0.2 | 0.1 | — | 0.2 |

TABLE 3-continued

| | D7 | D8 | D9 | D10 | D11 | D12 | D13 | D14 | D15 | D16 |
|---|---|---|---|---|---|---|---|---|---|---|
| Feed 3 | | | | | | | | | | |
| Styrene pphm[1)] | — | 20 | — | — | — | 20 | 20 | 20 | — | — |
| MMA pphm[1)] | 95 | 75 | 95 | 95 | 95 | 75 | 75 | 75 | 95 | 95 |
| DMAEMA pphm[1)] | 5 | 5 | 5 | 5 | 5 | 5 | 5 | 5 | 5 | 5 |

[1)]pphm: percent by weight based on the monomers present in the feed
MMA: methyl methacrylate
BDGA: butyl glycol diacrylate
AMA: allyl methacrylate
DMAEMA: dimethylaminoethyl methacrylate MMS: methyl methacrylate
BDGA: butyl glycol diacrylate
AMA: allyl methacrylate
DMAEMA: dimethylaminoethyl methacrylate All dispersions had mean particle sizes of below 100 nm. Dispersions D12, D13 and D14 displayed a core-shell morphology, the shell containing styrene (determined in a butyl methacrylate matrix by means of transmission electron microscopy and $RuO_4$-contrasting). All the other dispersions displayed a so-called blackberry morphology.

Application Evaluation:
Insecticidal Activity

The insecticidal action of the compositions was demonstrated by the following experiment:

The aqueous active ingredient composition according to the invention of Example 3 was diluted with water to three different active ingredient concentrations. For comparison purposes, the anionic dispersion D6, which is not in accordance with the invention, was studied, and α-cypermethrin was dissolved in acetone, and the solution was diluted with further acetone to give the active ingredient concentrations in question.

To determine the limits of the efficacy of the composition according to the invention with regard to wood-destroying soil-dwelling termites (*Reticulitermes santonensis*), wood specimens of *Pinus* spp. with the dimensions 25×25×6 mm³ (Southern Yellow Pine) were tested in accordance with the American test standard AWPA E1-97 (see, in this context, "Standard method for laboratory evaluation to determine resistance to subterranean termites", American Wood-Preservers' Association, 2001) under constrained experimental conditions after leaching according to DIN EN 84: 1997-01 (see, in this context, "accelerated aging of treated timber before biological tests", European standardization committee).

The destruction of the timber caused by attack by the termites was registered after 4 weeks of testing by visually scoring the timber specimens as specified in AWPA E1-97. In addition, the mortality rate among the termites was estimated.

If the timber specimens were still intact (having a score of 10 to 9 "sound-light attack" on a scale from 10 to 0), the protection of the timber obtained by the preservative at a specific active ingredient concentration is considered as sufficient.

A limit for α-cypermethrin after leaching of ≥20 g/m³ was determined for the aqueous cationic design of the active ingredient composition according to the invention. The timber is sufficiently protected at this minimum concentration (in the present case a score of 10 "sound, surface nibbles permitted"). The limit after leaching for the active ingredient which was dissolved in pure acetone for comparison purposes was 29-40 g/m³ (see Table 3).

TABLE 3

| Test termite: *R. santonensis* Dispersion | Limits of the efficacy [g/m³] after leaching (EN 84) |
|---|---|
| D5 | ≥20 |
| D6 | 21-33 |
| Solution of α-cypermethrin | 29-40 |

The assessment of a timber preservative under practice conditions relies in particular on the lower value after leaching. The results shown in Table 3 confirm that the cationic design of the active ingredient composition D5 according to the invention has a better activity against wood-destroying soil-dwelling termites than the corresponding anionic design of the formulation D6 or the pure active ingredient in an organic solvent.

We claim:

1. A method for protecting lignocellulosic materials against attack or destruction by harmful insects, comprising the treatment of the lignocellulosic material with an aqueous insecticide composition in the form of an aqueous dispersion of finely divided polymer particles which comprise at least one insecticidal organic active ingredient with a solubility in water of not more than 5 g/l at 25° C. at 1013 mbar, said polymer particles having a mean particle size, determined by dynamic light scattering, of not more than 500 nm, where the polymer particles which comprise the at least one insecticidal active ingredient have a positive surface charge and where the aqueous dispersion of the active-ingredient-comprising polymer particles is obtained by subjecting a monomer composition of ethylenically unsaturated monomers M, in which the ethylenically unsaturated monomers M comprise the at least one insecticidal active ingredient in dissolved form, to radical aqueous emulsion polymerization, wherein the insecticidal active ingredient is selected among pyrethroids, carbamates, organo(thio)phosphates, arthropod growth regulators, pyrazole insecticides, abamectin, acequinocyl, amidrazone, amidoflumat, amitraz, azadirachtin, bifenazate, cartap, chlorfenapyr, chlordimeform, cyromazine, diafenthiuron, diofenolan, enamectin, endosulfan, fenazaquin, formetanate, formetanate-hydrochloride, hydramethylnon, indoxacarb, metaflumizon (4-{(2Z)-2-({4-(trifluoromethoxy)anilinol] carbonyl} hydrazono)-2-[3-trifluoromethyl)phenyl]ethyl}benzonitrile), pyridaben, pymetrozine, spinosad, tebufenpyrad, flupyrazaphos, flonicamid, flufenerim, flubendiamide, bistrifluron, NC512, benclothiaz, cyflumethofen, milbermectin, cyclometofen, lepimectin, profluthrin, dimefluthrin, N-ethyl-2,2-dichloro-1-methylcyclopropanecarboxamide-2-(2,6-dichloro-α,α,α-trifluroro-p-tolyl)phydrazone, N-ethyl-2,2-dimethylpropionamide-2-(2,6- dichloro-4-trifluoromethylphenyl)hydrazone, thiocyclam, pyridalyl, spirotetramat and neonicotinoids, wherein the monomers M comprise from 0.1 to 20% by weight based on the total amount of the monomers M of at least one monoethylenically unsaturated monomer M-k which is selected among monomers of the general formula I

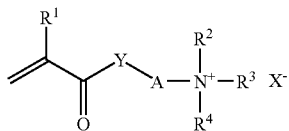

in which $R^1$ is hydrogen or $C_1$-$C_4$-alkyl, $R^2$, $R^3$ independently of one another are $C_1$-$C_4$-alkyl and $R^4$ is hydrogen or $C_1$-$C_4$-alkyl, Y represents oxygen, NH or $NR^5$ wherein $R^5$ is $C_1$-$C_4$-alkyl, A represents $C_2$-$C_8$-alkylene which is optionally interrupted by 1, 2 or 3 non-adjacent oxygen atoms, and $X^-$ represents an anion equivalent;

wherein the monomers M further comprise from 60 to 99% by weight, based on the total amount of the monomers M, of at least one neutral monoethylenically unsaturated monomer M1 with a solubility in water of not more than 60 g/l at 25° C., which is selected from the group consisting of vinyl-aromatic monomers, $C_2$-$C_{10}$-alkyl acrylate and $C_1$-$C_{10}$-alkyl methacrylates.

2. The method according to claim 1, wherein the lignocellulosic material is timber.

3. A method for protecting lignocellulosic materials against attack or destruction by harmful insects, comprising the treatment of the lignocellulosic material with a pulverulent insecticide composition obtained by drying an aqueous insecticide composition as defined in claim 1.

4. The method according to claim 3, wherein the lignocellulosic material is timber.

5. The method according to claim 1 or claim 3, wherein the aqueous dispersion of the active-ingredient-comprising polymer particles is obtained by radical aqueous emulsion polymerization of the monomer composition in the presence of a cationic surface-active substance.

6. The method according to claim 1 or claim 3, wherein the aqueous insecticide composition comprises the at least one insecticidal active ingredient in an amount of from 0.1 to 50% by weight, based on the weight of the monomers M employed for the preparation of the polymer.

7. The method according to claim 1 or claim 3, wherein the insecticidal active ingredient is selected among pyrethroids, carbamates, organo(thio)phosphates, arthropod growth regulators, chlorfenapyr and neonicotinoids.

8. The method according to claim 1 or claim 3, wherein the polymer particles do not comprise fungicidal active ingredients.

9. The method according to claim 1 or claim 3, wherein the aqueous insecticide composition contains less than 1% by weight, based on the total weight of the composition, of volatile organic components.

10. The method according to claim 1 or claim 3, wherein the aqueous insecticide composition contains solids in an amount of from 10 to 60% by weight.

11. The method according to claim 1 or claim 3, wherein the monomers M comprise from 1 to 20% by weight based on the total amount of the monomers M of at least one monoethylenically unsaturated monomer M-k.

12. The method according to claim 1 or claim 3, wherein the monomers M comprise from 80 to 99% by weight, based on the total amount of the monomers M, of at least one neutral monoethylenically unsaturated monomer M-1.

13. The method according to claim 1 or claim 3, wherein monomers M-k and M1 together constitute 100% by weight based on the total amount of the monomers M.

14. The method according to 1 or claim 3, wherein the polymer has a glass transition temperature $T_G$ of at least 10° C.

* * * * *